(12) United States Patent
Riedel et al.

(10) Patent No.: US 10,888,667 B2
(45) Date of Patent: Jan. 12, 2021

(54) INJECTION DEVICE WITH SUPPLEMENTARY DEVICE

(71) Applicant: SANOFI-AVENTIS DEUTSCHLAND GMBH, Frankfurt am Main (DE)

(72) Inventors: Stephan Riedel, Frankfurt am Main (DE); Pauline Mannechez, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 15/551,985

(22) PCT Filed: Feb. 19, 2016

(86) PCT No.: PCT/EP2016/053590
§ 371 (c)(1),
(2) Date: Aug. 18, 2017

(87) PCT Pub. No.: WO2016/131974
PCT Pub. Date: Feb. 5, 2016

(65) Prior Publication Data
US 2018/0028759 A1    Feb. 1, 2018

(30) Foreign Application Priority Data

Feb. 19, 2015 (EP) .................................... 15155757

(51) Int. Cl.
*A61M 5/315* (2006.01)
*A61M 5/31* (2006.01)
*A61M 5/32* (2006.01)

(52) U.S. Cl.
CPC .......... *A61M 5/31566* (2013.01); *A61M 5/31* (2013.01); *A61M 5/3155* (2013.01);
(Continued)

(58) Field of Classification Search
CPC ................ A61M 5/31566; A61M 5/31; A61M 2205/50; A61M 2205/502;
(Continued)

(56) References Cited

U.S. PATENT DOCUMENTS

| 9,827,379 B2 | 11/2017 | Veasey et al. |
| 2004/0010233 A1 | 1/2004 | Hjertman et al. |

(Continued)

FOREIGN PATENT DOCUMENTS

| CN | 1780652 | 5/2006 |
| CN | 101501459 | 8/2009 |

(Continued)

OTHER PUBLICATIONS

International Preliminary Report on Patentability in International Application No. PCT/EP2016/053590, dated Aug. 22, 2017, 4 pages.

(Continued)

*Primary Examiner* — Nilay J Shah
(74) *Attorney, Agent, or Firm* — Fish & Richardson P.C.

(57) ABSTRACT

A supplementary device for a manually operable injection device, the supplementary device including a body having at least one engaging member to releasably mount the body to the injection device in a specific position on an outside surface of the injection device, and at least one indicator located on the body and having a shape or contour to overlap or to align with a mark on the outside surface of the injection device when the body is in or near the specific position.

16 Claims, 7 Drawing Sheets

(52) U.S. Cl.
CPC ... *A61M 5/3202* (2013.01); *A61M 2005/3125* (2013.01); *A61M 2005/3126* (2013.01); *A61M 2205/3306* (2013.01); *A61M 2205/3375* (2013.01); *A61M 2205/50* (2013.01); *A61M 2205/502* (2013.01); *A61M 2205/52* (2013.01); *A61M 2205/581* (2013.01); *A61M 2205/582* (2013.01); *A61M 2205/60* (2013.01); *A61M 2205/6072* (2013.01); *A61M 2205/6081* (2013.01)

(58) Field of Classification Search
CPC .......... A61M 2205/52; A61M 2209/04; A61M 2005/006; A61M 2205/60; A61M 2205/6036; A61M 2205/6045; A61M 2205/6063; A61M 2205/6081; A61M 2005/3125; A61M 2005/3126
See application file for complete search history.

(56) References Cited

U.S. PATENT DOCUMENTS

| | | | |
|---|---|---|---|
| 2004/0057855 A1* | 3/2004 | Gerlach | A61M 5/142 417/469 |
| 2009/0224004 A1 | 9/2009 | Muller et al. | |
| 2010/0036320 A1 | 2/2010 | Cox et al. | |
| 2011/0295215 A1* | 12/2011 | Nielsen | G16H 20/17 604/257 |
| 2011/0313349 A1* | 12/2011 | Krulevitch | A61M 5/24 604/65 |
| 2013/0041346 A1* | 2/2013 | Alon | A61M 5/20 604/506 |
| 2013/0096510 A1 | 4/2013 | Plumptre et al. | |
| 2013/0274661 A1 | 10/2013 | Teucher et al. | |
| 2014/0012227 A1 | 1/2014 | Sigg et al. | |
| 2014/0249482 A1 | 9/2014 | Wieselblad | |

FOREIGN PATENT DOCUMENTS

| | | |
|---|---|---|
| CN | 102413856 | 4/2011 |
| CN | 104010677 | 8/2014 |
| CN | 104427972 | 3/2015 |
| JP | 2009-540986 | 11/2009 |
| JP | 2011-530337 | 12/2011 |
| JP | 2012-504440 | 2/2012 |
| JP | 2012-519025 | 8/2012 |
| JP | 2014-515947 | 7/2014 |
| WO | WO 2007/107431 | 9/2007 |
| WO | WO 2008/003560 | 1/2008 |
| WO | WO 2009/024562 | 2/2009 |
| WO | WO 2010/017285 | 2/2010 |
| WO | WO 2010/037828 | 4/2010 |
| WO | WO 2010/098927 | 9/2010 |
| WO | WO 2010/098928 | 9/2010 |
| WO | WO 2011/131776 | 10/2011 |
| WO | WO 2012/152700 | 11/2012 |
| WO | WO 2013/120773 | 8/2013 |
| WO | WO 2013/120775 | 8/2013 |
| WO | WO-2013120775 A1 * | 8/2013 ............. A61M 5/24 |
| WO | WO 2014/173773 | 10/2014 |
| WO | WO-2014173773 A1 * | 10/2014 ............. A61M 5/24 |

OTHER PUBLICATIONS

International Search Report and Written Opinion in International Application No. PCT/EP2016/053590, dated Jun. 3, 2016, 8 pages.

* cited by examiner

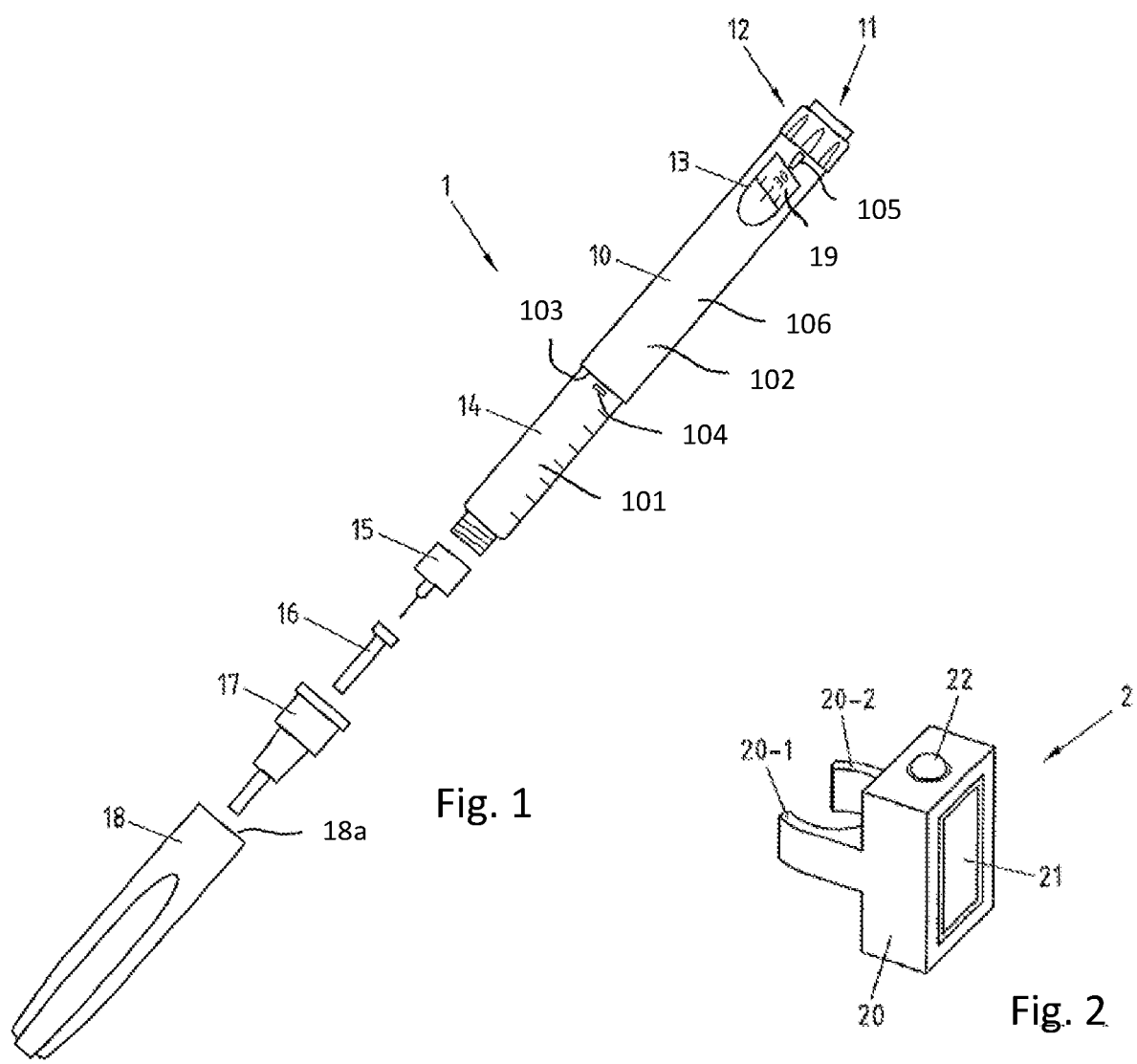
Fig. 1
Fig. 2
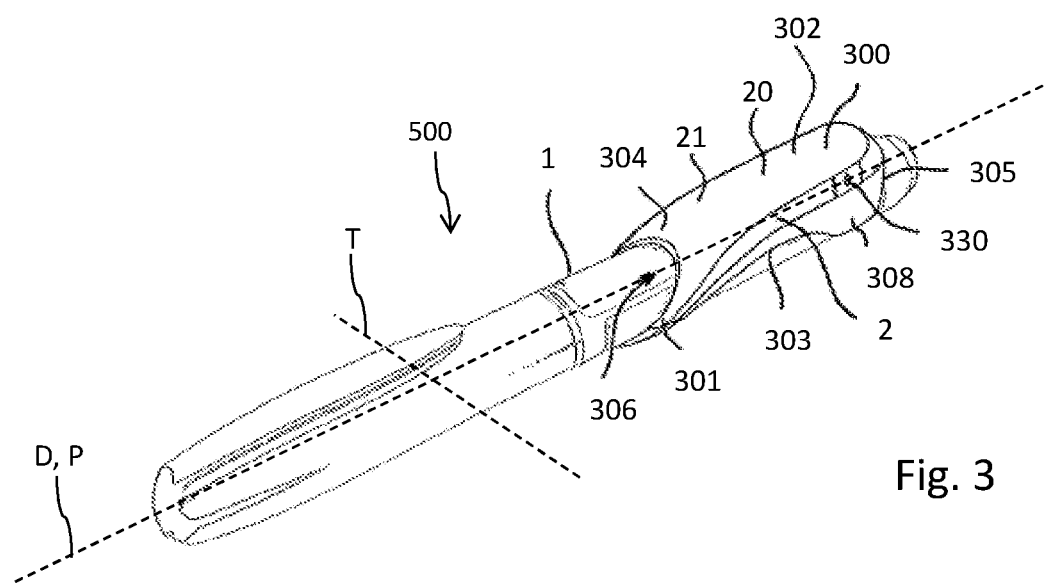
Fig. 3

INJECTION DEVICE WITH SUPPLEMENTARY DEVICE

CROSS REFERENCE TO RELATED APPLICATIONS

The present application is the national stage entry of International Patent Application No. PCT/EP2016/053590, filed on Feb. 19, 2016, and claims priority to Application No. EP 15155757.6, filed in on Feb. 19, 2015, the disclosures of which are expressly incorporated herein in entirety by reference thereto.

TECHNICAL FIELD

The present disclosure relates to an apparatus for supplementing a medical device configured to eject a medicament. In particular, the present disclosure relates to a supplementary device for a manually operable injection device

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dosage knob and observing the actual dose from a dose window or display of the insulin pen. The dose is then injected by inserting the needle into a suited skin portion and pressing an injection button of the insulin pen.

To be able to monitor insulin injection, for instance to prevent false handling of the insulin pen or to keep track of the doses already applied, it is desirable to measure information related to a condition and/or use of the injection device, such as for instance information on the injected insulin type and dose. In this respect, WO 2009/024562 discloses a medical device with a value sensor. A Radio Frequency Identification (RFID) unit includes a value sensor such as a pressure sensor and is integrated with a liquid medicament container to enable wireless pressure or other medicament relevant parameter value monitoring. The liquid medicament container is coupled with a first housing part of the medical device, which first housing part may for instance constitute a pre-filled disposable injection device. The RFID unit communicates wirelessly with a control circuit that is contained in a second housing part of the medical device that is releasably attached to the first housing part. The control circuit is adapted to process the values measured by the RFID unit, to compare it with pre-defined values and to provide an alert to the user if the measured values fall outside normal operating conditions, and to communicate data relating to the measured values to an external device for further data processing.

Furthermore, document WO 2013/120775 A1 describes an electronic clip-on module for a manually operable pen-type injection device. The module configured as a supplementary device has a body and a mating unit configured to releasably mount the body to the injection device in a specific position relative to an outside surface of the injection device for a secure and releasable fastening of the supplementary device to the injection device. A rib protrudes from the outer surface of the injection device that acts as an alignment element for locating a body of the supplementary device in a specific position relative to the outer surface of the injection device.

When properly aligned the rib will be received in a rib-receiving recess in the body of the supplementary device. The supplementary device further includes protuberances to releasably engage in corresponding indents of the housing of the injection device. When the supplementary device mates correctly with the injection device a haptic feedback from the mating of the protuberances with the indents is provided. But when the supplementary device is not correctly aligned with the injection device in a longitudinal direction or in a circumferential or tangential direction the rib and the rib-receiving recess as well as the protuberances and the indents will not be aligned but will be located offset from each other.

In such a configuration the supplementary device cannot be mounted to the injection device. Moreover, since the mutually mating structures, namely rib-receiving recesses as well as protuberances and indents may not visible to the user during the progress of mounting the supplementary device to the injection device a correct alignment and orientation for finally attaching and mounting the supplementary device to the injection device might be somewhat cumbersome and annoying.

In one aspect, the present disclosure provides an improved supplementary device that is releasably mountable or releasably attachable to a manually operable injection device in a rather simple, straight forward and intuitive way. The present disclosure may provide a correspondingly configured manually operated injection device that provides and supports facilitated, easy and straight forward releasable attachment of the supplementary device thereto. The improvements should be rather easy implementable into the design of existing supplementary devices and injection devices. In this regard the improvements according to the present disclosure are retrofittable to existing supplementary devices and corresponding injection devices. In another aspect, the present disclosure provides a kit comprising an injection device and a correspondingly configured supplementary device that allow and support a visual or haptic control of the attachment procedure when mounting the supplementary device to the injection device.

SUMMARY

In a first aspect of embodiments of the disclosure there is provided a supplementary device for a manually operable injection device. The supplementary device includes a body having at least one engaging member to releasably mount or to releasably engage the body to the injection device in a specific position on an outside surface of the injection device. Typically, the engaging member of the body of the supplementary device is releasably engageable with at least one correspondingly or complementary-shaped engaging member on an outside facing portion of a housing of the injection device. Typically, mutually corresponding engaging members of the body of the supplementary device and of the housing of the injection device provide a positive engagement, such like a snap-fit or clip-like engagement. Alternatively, the mutually corresponding engaging members are configured to provide a frictional engagement of the body of the supplementary device and the housing of the injection device.

On the body of the supplementary device there is at least provided one indicator having a shape or contour to overlap or to align with a mark on the outside surface of the injection device when the body is in or near the specific position on the outside surface of the injection device. Mutually corresponding indicators and marks provide a rather intuitive approach to indicate to the user, that the body of the supplementary device and the housing of the injection device are correctly aligned and oriented prior to conducting a fastening or mounting procedure. Typically, the at least one indicator is located remote, hence at a non-zero distance from the engaging member of the body. Correspondingly, also the at least one mark on the outside surface of the injection device is located remote, hence at a non-zero distance, from the at least one engaging member of the housing of the injection device.

The indicator and the mark are located on the body and the housing of the injection device in addition to the mutually corresponding engaging members of body and injection device. Typically, the at least one indicator or the mark are permanently visible or perceptible by the user during an attachment or mounting of the supplementary device to the injection device.

In particular, the supplementary device and the injection device are arrangeable in a preassembly configuration, in which the supplementary device is already in mechanical or physical contact with the housing of the injection device but in which the supplementary device is at least rotatable or longitudinally translationally displaceable relative to the injection device; and vice versa. In such a preassembly configuration the supplementary device is alignable and orientable relative to the injection device with the aid of the at least one indicator and the at least one mark. In the preassembly configuration the body of the engaging member is displaceable, hence longitudinally displaceable or rotatable relative to the injection device to bring the at least one indicator of the supplementary device into a geometric overlapping configuration with the at least one mark on the outside surface of the injection device. If the at least one indicator overlaps or aligns with the at least one mark the supplementary device and the injection device are correctly aligned. In such a correct alignment configuration the supplementary device is transferrable into an end assembly configuration in which it is typically rotationally and translationally fixed to the injection device.

According to another embodiment the indicator includes an aperture or a recess in the body of the supplementary device. A recess may be formed in a border region or in an outer edge of the body while an aperture may be provided in the bulk of the body, hence at a certain distance from a border or margin of the body of the supplementary device. The aperture in the body of the supplementary device is typically located in a sidewall portion of the body. The aperture reveals a section of the outside surface of the injection device located underneath the supplementary device when supplementary device and injection device are in the preassembly configuration. When implemented as a recess in a margin or border region of the body the recess may include a V-shaped geometry with a pointed tip extending inwardly, i.e. away from the border or margin.

Alternatively, it is also conceivable that the indicator includes a protrusion extending in a longitudinal direction from a longitudinal end or border section of the body. In addition or alternatively it is also conceivable, that the indicator just includes an indicator mark in or on a transparent section of the body of the supplementary device. For a correct and proper alignment of supplementary device and injection device it is then only required to bring the indicator mark into a substantially overlapping configuration with the at least one mark on the outside surface of the injection device. Typically, the indicator is located at a well-defined specific position on the body of the supplementary device. In addition, also the mark corresponding to or matching with the indicator is located at a well-defined and specific position on the outside surface of the injection device, typically on the outside surface of the housing of the injection device.

The position of the indicator with regard to the circumference or tangential direction and/or with regard to a longitudinal direction of the body as well as the specific position of the at least one mark with regard to the tangential or circumferential direction and/or the longitudinal direction of the housing of the injection device is selected such, that the supplementary device and the injection device correctly align in the specific position when the at least one indicator overlaps or aligns with the at least one mark.

According to another embodiment the contour of the aperture or recess matches with the shape of the mark. For instance, if the aperture is circular symmetric also the aperture includes a circle or a circular dot having a geometry and contour that substantially matches with the contour and geometry of the aperture. The same is valid for the recess. If the recess is for instance V-shaped and extends from a margin or border of the body of the supplementary device also the mark provided on the outside surface of the injection device includes a somewhat triangular or V-shaped structure that matches in size and geometry with the recess.

In addition or alternatively it is conceivable that the mark includes a rather large extension on the outside surface of the injection device but exhibits a center that is visually detectable. For instance, the mark may include a cross, wherein a crossing point of at least two lines that form said cross defines the center of the mark. For a proper and correct alignment of supplementary device and injection device it is then only intended to arrange the center of the mark in the center of the aperture or of a correspondingly-shaped recess.

Generally, the contours of the indicators and corresponding marks can be arbitrarily chosen as long as the body of the supplementary device and the injection device are displaceable or rotatable relative to each other to bring the indicator and the mark in a mutually overlapping or mutually aligned configuration that corresponds to the correct alignment and orientation of the supplementary device and the injection device.

According to another embodiment the indicator is arranged on a collar of the body, which collar is configured to receive the injection device so that the injection device extends through the collar. Typically, the collar and the body are integrally formed. Body and collar may be made of a single piece of an injection molded plastic component. The collar typically forms an aperture into which the housing of the injection device is displaceable along a longitudinal direction. A residual portion of the body is typically configured to get in radial abutment with an outside surface of the injection device. Typically, the injection device is of pen-injector type and includes a substantially tubular-shaped housing and hence a correspondingly and tubular-shaped outside surface.

Due to the collar and arranging the injection device in said collar embracing the outer circumference of the injection device the injection device and the collar, hence the injection device and the body of the supplementary device are inherently fixable relative to each other with regard to a radial direction. Hence, a preassembly configuration of injection device and supplementary device is obtainable simply by inserting the housing of the injection device into and through the collar of the supplementary device. In the preassembly configuration the injection device is rotatable with regard to its longitudinal axis relative to the supplementary device. Furthermore, the injection device is also displaceable with regard to the longitudinal direction relative to the supplementary device. Typically, the collar is not subject to a transient or temporal deformation during the mutual assembly of supplementary device and injection device. It is therefore of particular advantage to arrange the at least one indicator on or in the collar of the body.

According to another embodiment the collar extends from a first longitudinal end and from a lower side of the body. The at least one engaging member of the body is however located at or near a second longitudinal end of the body that is located opposite to the first longitudinal end.

In this way, and when the indicator is arranged in or on the collar, indicator and engaging member of the body are located at oppositely located longitudinal ends of the body. Such a configuration is of particular benefit when the fastening or mounting of the supplementary device to the injection device requires a pivoting or rotation of the supplementary device relative to the injection device with regard to a transverse axis that extends substantially perpendicular to the longitudinal axis of the body of the supplementary device or of the housing of the injection device.

Then, the second longitudinal end of the body may be subject to a non-neglectable radial displacement relative to the housing of the injection device when transferring the supplementary device from the preassembly configuration towards and into the end assembly configuration. By providing the indicator on an opposite longitudinal end of the body, e.g. near a front end the degree of a radial displacement of the indicator relative to the housing of the injection device may be much smaller than a radial displacement of the engaging member of the body of the supplementary device relative to a correspondingly-shaped engaging member of the injection device that are typically located at the opposite longitudinal end, e.g. at or near a rear end. In this way, the indicator being in an overlapping configuration with the mark will not be subject to a substantial displacement when transferring the supplementary device from a preassembly configuration towards and into the end assembly configuration.

According to another embodiment the body is rotatable relative to the injection device about a transverse axis extending through the collar and extending perpendicular to the longitudinal axis of the injection device or extending perpendicular to the longitudinal axis of the body. In such an embodiment the indicator is much closer to the transverse axis than the engaging member of the body. While the engaging member of the body may be subject to a substantial radial displacement when transferring the supplementary device from the preassembly configuration into the end assembly configuration the position of the indicator relative to the mark may remain substantially fixed.

According to a further embodiment the collar includes an aperture to surround the outer surface of the injection device. Here, an inner cross-section or an inner diameter of the aperture is larger than an outer cross-section or an outer diameter of the injection device. Alternatively it is conceivable, that at least a portion of the aperture of the collar is slanted or chamfered in order to support a pivoting of the body and hence of the collar integrally formed therewith relative to the housing of the injection device. When the inner diameter or cross-section of the aperture is at least slightly larger than the outer circumference or outer cross-section of the injection device the injection device can be inserted in longitudinal direction into and through said aperture in such a way that a pivoting of the body relative to the injection device with regard to the transverse axis is still possible to a desired degree.

In another embodiment the collar includes an upper part and a lower part. The upper part is connected to or is integrally formed with the body, wherein that portion of the body being integrally formed with the upper part of the collar extends towards the second longitudinal end. In this way, the body forms a kind of a shell to clamp around or along a portion of the outer circumference of the outside surface of the injection device. This part of the body particularly serves or includes a housing for the supplementary device to house various electronic components to interact with mechanical components of the injection device, in particular with a mechanically implemented display of the injection device.

In another embodiment of the supplementary device the body includes two wings extending from the lower side of the body and forming a channel therebetween to receive the injection device. The wings include a lower border facing away from the body. These lower borders of the wings further extend in longitudinal direction into a lower border of the collar and form the recess constituting the indicator of the supplementary device. The lower border of the collar, typically facing towards the second longitudinal end of the body, may smoothly extend into the lateral wings extending from the lower side of the body. In this way the lower borders of the wings together with the lower border of the collar form a somewhat U-shaped bordering structure when viewing the supplementary device from below. In this case, the recess forming the indicator is defined by the border of a lower lateral side of the body, which recess can be regarded as the margins of a sidewall obtained by cutting away a portion from a cylindrically-shaped body.

In another embodiment the supplementary device includes an optical reading arrangement arranged at a lower side of the body at a first specific distance to the at least one indicator. This first specific distance, which includes a longitudinal distance as well as a circumferential or tangential distance along the inner circumference of the body or along the outer circumference of the outside surface of the housing of the injection device corresponds to or is equal to a second specific distance between a display of the injection device and the at least one mark on the outside surface of the injection device. Also the second specific distance includes a longitudinal distance between the display and the at least one mark as well as a circumferential or tangential distance between the display and the at least one mark when assuming that the outside surface of the injection device is substantially tubular-shaped.

With this definition of first and second specific distances it is clear that the optical reading arrangement of the supplementary device substantially overlaps and is correctly aligned with the display of the injection device when the at least one indicator of the body substantially overlaps or aligns with the at least one mark on the outside surface of the injection device. This overlapping or alignment of indicator and mark may be obtained prior to an end assembly configuration of supplementary device and injection device.

In another aspect the disclosure also relates to a manually operable injection device. The injection device includes a housing with at least one engaging member to releasably mount a supplementary device as described above in a specific position on an outside surface of the housing. The injection device further includes at least one mark on the outside surface to overlap or to align with an indicator of the supplementary device when the supplementary device is in or near the specific position.

The manually operable injection device is particularly configured to cooperate with the supplementary device as described above. Hence, the manually operable injection device includes all those features that are necessary and that have already been mentioned in connection with the supplementary device as described above.

According to a further embodiment the at least one mark on the outside surface of the housing is a visual mark and includes a shape or contour that matches with the shape or contour of the indicator of the supplementary device. The visual mark may include or consist of a simple geometric structure, such like a point, a circle, a quadratic or rectangular symbol, a triangle or any other arbitrarily-shaped symbol matching with the shape or contour of the indicator.

According to another embodiment the at least one mark is a haptic mark and forms a protrusion or a recess on the outside surface of the housing of the injection device. Making use of a perceptible touchable protrusion or recess as a mounting and centering aid for the supplementary device is of particular use for users or patients that suffer impaired vision.

Due to such a haptic mark, the supplementary device and the injection device are displaceable in longitudinal as well as rotatable in a tangential direction until the indicator comprising a recess or protrusion matching with the protrusion or recess of the haptic mark, engages therewith, thereby haptically indicating to the user, that a correct alignment configuration of supplementary device and injection device has been reached. In a proceeding step the user may then perform and conduct the end assembly of the supplementary device and the injection device in a rather precise and successful way.

According to another embodiment the mark is integrated into a label that is adhesively attached to the outside surface of the injection device. Such an integration of a mark is particularly possible with visual marks. By integrating the mark into a label existing injection devices may be retrofitted with a respective mark. Moreover, a set of differently configured labels can be provided, e.g. labels having different marks at different positions, each of which corresponding to differently configured supplementary devices. In this way differently configured supplementary devices can be universally combined with a large variety of injection devices simply by selecting an appropriate label having a specific mark thereon that matches and corresponds to the supplementary device of choice. The attachment of a specific mark on the outside surface of the injection device does therefore not require a redesign of the outer shape or contour of an existing injection device.

The integration of the mark into a label is also conceivable with haptic marks, wherein the haptic mark is constituted by protrusion on the label or by a recess in the label. In the latter case the label includes a particular thickness to provide a recess of sufficient depth.

Furthermore and according to another aspect the disclosure also relates to a kit comprising an injection device as described above and further comprising a supplementary device as further described above. It is particularly conceivable that the injection device is of disposable type whereas the supplementary device is releasably attachable to a series or a sequence of injection devices.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound includes at least one peptide for the treatment and/or prophylaxis of diabetes mellitus or complications associated with diabetes mellitus such as diabetic retinopathy, wherein in a further embodiment the pharmaceutically active compound includes at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivatives are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,

H-(Lys)5-des Pro36, des Pro37 Exendin-4(1-39)-NH2, des Pro36 Exendin-4(1-39), des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28] Exendin-4(1-39), des Pro36 [Met(O)14 Trp(O2)25, IsoAsp28] Exendin-4(1-39);

or des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28] Exendin-4(1-39), des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence des Pro36 Exendin-4(1-39)-Lys6-NH2 (AVE0010), H-(Lys)6-des Pro36 [Asp28] Exendin-4(1-39)-Lys6-NH2, des Asp28 Pro36, Pro37, Pro38 Exendin-4(1-39)-NH2, H-(Lys)6-des Pro36, Pro38 [Asp28] Exendin-4(1-39)-NH2, H-Asn-(Glu)5des Pro36, Pro37, Pro38 [Asp28] Exendin-4(1-39)-NH2, des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention. Further, it is to be noted, that any reference numerals used in the appended claims are not to be construed as limiting the scope of the invention.

BRIEF DESCRIPTION OF THE FIGURES

In the following, embodiments of the drive mechanism and the injection device are described in detail by making reference to the figures, in which:

FIG. 1 schematically shows a manually operable injection device,

FIG. 2 shows a schematic illustration of a supplementary device to be releasably attached to the injection device of FIG. 1, FIG. 3 shows a perspective view of the supplementary device of FIG. 2 releasably attached to the injection device of FIG. 1.

DETAILED DESCRIPTION

Figure 4:
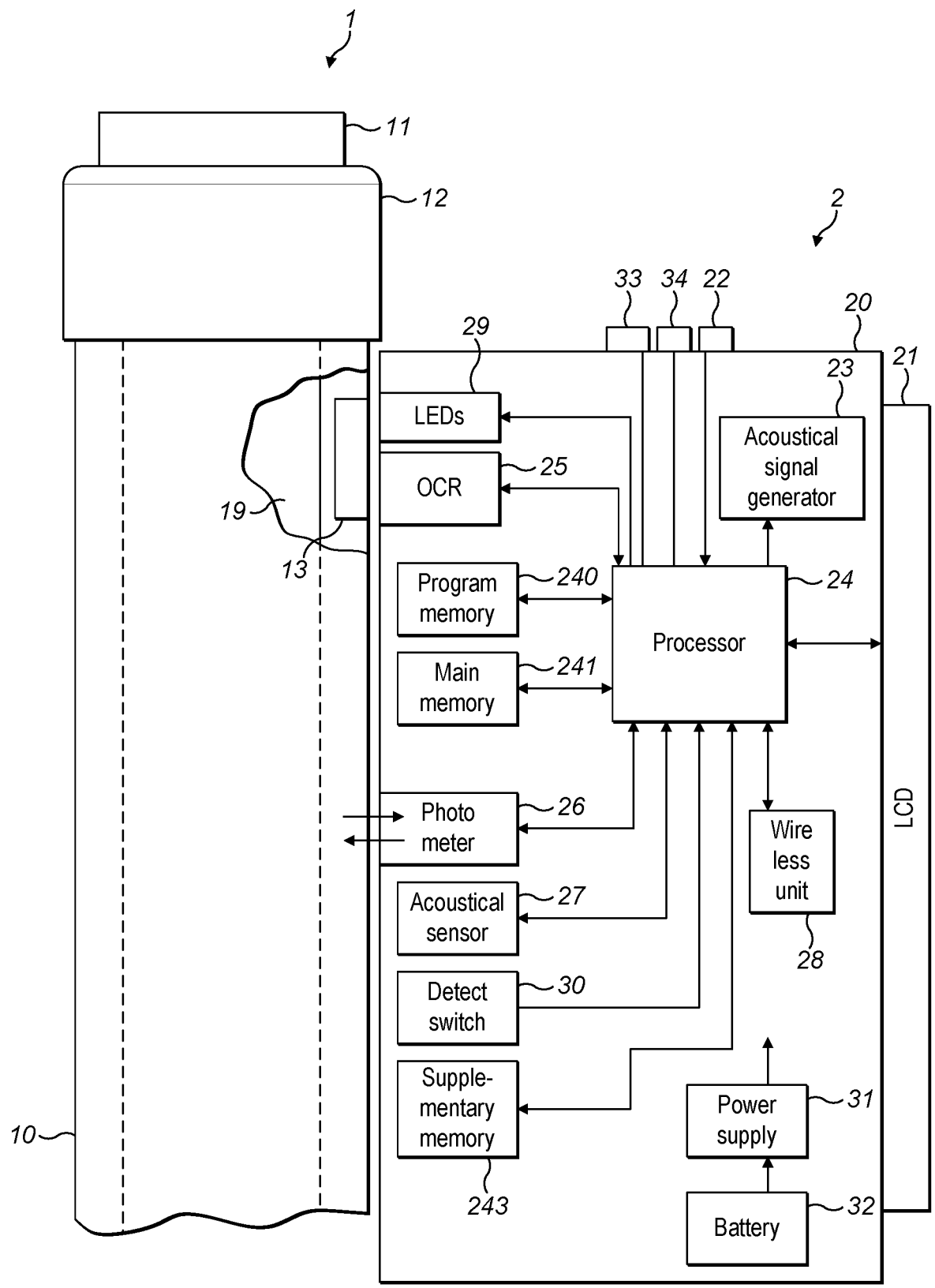
FIG. 4 shows a schematic view of the supplementary device in a state where it is mounted to the injection device.

FIG. 1 is an exploded view of an injection device 1, which may for instance represent Sanofi's Solostar® insulin injection pen.

The injection device 1 of FIG. 1 is a pre-filled, disposable injection pen that includes a housing 10 and contains an insulin container 14, to which a needle 15 can be affixed. The needle is protected by an inner needle cap 16 and an outer needle cap 17, which in turn can be covered by a cap 18. An insulin dose to be ejected from injection device 1 can be selected by turning a dosage knob 12, and the selected dose is then displayed via a dosage window or display 13, for instance in multiples of so-called International Units (IU), wherein one IU is the biological equivalent of about 45.5 micrograms of pure crystalline insulin (1/22 mg). An example of a selected dose displayed in dosage window or display 13 may for instance be 30 IUs, as shown in FIG. 1. It should be noted that the selected dose may equally well be displayed differently, for instance by an electronic display. It will be understood that dosage window relates to the section of the injection device through or on which the selected dosage is visible.

Turning the dosage knob 12 causes a mechanical click sound to provide acoustical feedback to a user. The numbers displayed in dosage window or display 13 are printed on a sleeve 19 that is contained in housing 10 and mechanically interacts with a piston in the insulin container 14. When needle 15 is stuck into a skin portion of a patient, and then injection button 11 is pushed, the insulin dose displayed in display 13 will be ejected from injection device 1. When the needle 15 of injection device 1 remains for a certain time in the skin portion after the injection button 11 is pushed, a high percentage of the dose is actually injected into the patient's body. Ejection of the insulin dose also causes a mechanical click sound, which is however different from the sounds produced when using dosage knob 12.

Injection device 1 may be used for several injection processes until either insulin container 14 is empty or the expiration date of injection device 1 (e.g. 28 days after the first use) is reached. Furthermore, before using injection device 1 for the first time, it may be necessary to perform a so-called "prime shot" to remove air from insulin container 14 and needle 15, for instance by selecting two units of insulin and pressing injection button 11 while holding injection device 1 with the needle 15 upwards. For simplicity of presentation, in the following, it will be exemplarily assumed that the ejected doses substantially correspond to the injected doses, so that, for instance when making a proposal for a dose to be injected next, this dose equals the dose that has to ejected by the injection device. Nevertheless, differences (e.g. losses) between the ejected doses and the injected doses may of course be taken into account.

The housing 10 of the injection device 1 includes a front section 101 and a rear section 102. The needle 15 is affixed to the front end of the front section 101 and the dosage knob 12 extends from the rear end of the rear section 102. The front section 101 has a smaller diameter than the rear section 102 of the injection device housing 10.

A shoulder 103 is defined between the front section 101 and the rear section 102. The shoulder 103 extends circumferentially around the housing 10. The cap 18 extends over the front section 101. The cap 18 covers the front section 101 and a lip 18a of the cap 18 locates against the shoulder 103.

A cap retaining ridge 104 is formed on the outer surface of the front section 101 of the housing 10 of the injection device 1. The cap retaining ridge 104 is disposed proximate to, but spaced from, the shoulder 103. The ridge 104 extends diametrically about the front section 101. The ridge 104 locates over one or more retaining elements (not shown) formed on the inner surface of the cap 18 to retain the cap 18 in position over the front section 101. Alternatively, the cap retaining ridge 104 locates in a corresponding diametrically extending recess (not shown) formed on the inner surface of the cap 18.

The injection device 1 further includes additional elements. A rib 105 protrudes from an outer surface 106 of the injection device 1. The rib 105 acts as an alignment element for locating the body in a specific position relative to the outer surface 106 of the injection device 1. The rib 105 upstands from the outer surface 106 of the injection device 1 between the dosage display 13 and the dosage knob 12. The dosage knob 12 is disposed on the rear section 102 of the injection device housing 10. The rib 105 is elongate and extends parallel to the longitudinal axis of the injection device 1.

Left and right indents 107 (refer to FIG. 6) are formed in the outer surface 106 of the injection device 1. The two indents 107 are formed in the rear section 102. Each indent 107 is formed proximate to the rear end of the injection device housing 10. The indents 107 are formed generally diametrically opposite to each other on left and right sides of the injection device 1. The indents 107 have chamfered sides.

FIG. 2 is a schematic illustration of an embodiment of a supplementary device 2 to be releasably attached to injection device 1 of FIG. 1. Supplementary device 2 includes a housing 20 with a mating unit configured to embrace the housing 10 of injection device 1 of FIG. 1, so that supplementary device 2 sits tightly on housing 10 of injection device 1, but is nevertheless removable from injection device 1, for instance when the injection device 1 is empty and has to be replaced. FIG. 2 is highly schematic, and details of one embodiment of the physical arrangement are described below with reference to FIG. 3. The wings or clip features 20-1 and 20-2 as shown in FIG. 2 generally represent engaging members 340 by way of which the supplementary device 2 is releasably attachable to the outer surface of the injection device 2.

Figure 8:
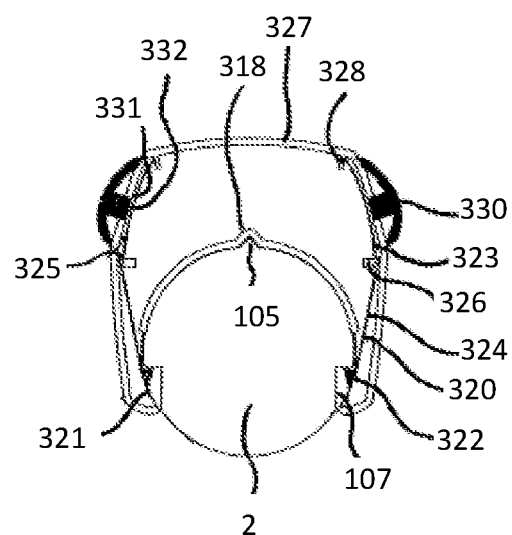
FIG. 8 shows a cross-sectional rear view of the supplementary device releasably attached to the injection device with resilient arms of a fixing unit in an engaged position with the injection device.
Figure 10:
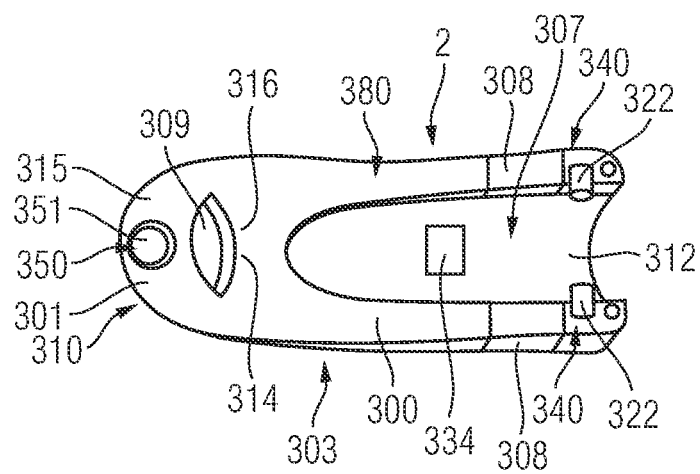
FIG. 10 shows a view of the lower side of the supplementary device according to one embodiment of the disclosure.
Figure 11:
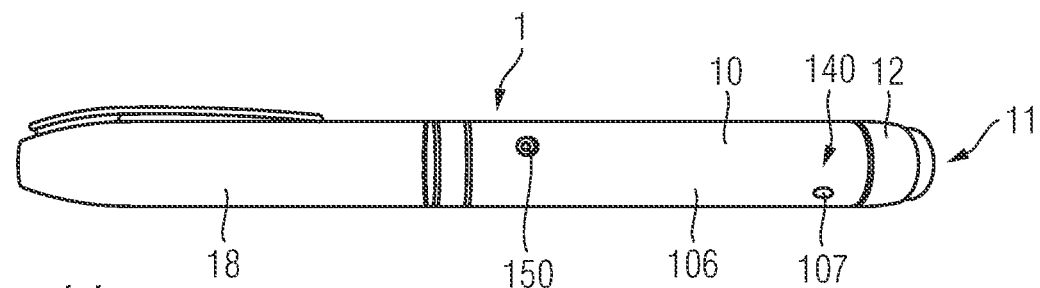
FIG. 11 shows a side view of one embodiment of the injection device with a mark.

The engaging members 340, 140 as shown in FIGS. 8, 10 and 11 may be generally realize din many different ways, e.g. by mutually engaging positive interlock means, such like resilient clip members.

Supplementary device 2 contains optical and acoustical sensors for gathering information from injection device 1. At least a part of this information, for instance a selected dose (and optionally a unit of this dose), is displayed via display unit 21 of supplementary device 2. The dosage display 13 of injection device 1 is obstructed by supplementary device 2 when attached to injection device 1.

Supplementary device 2 further includes three user input transducers, illustrated schematically as a button 22. These input transducers 22 allow a user to turn on/off supplementary device 2, to trigger actions (for instance to cause establishment of a connection to or a pairing with another device, and/or to trigger transmission of information from supplementary device 2 to another device), or to confirm something.

FIG. 3 shows a view of the supplementary device 2 with the arrangement of the mating unit and housing shown in greater detail. The supplementary device 2 is shown mounted to the injection device 1 in FIG. 3 thereby forming a kit 500 including the injection device 1 and the supplementary device 2. The housing 20 of the supplementary device 2 has a body 300 and a collar 301. The body 300 is elongate and the display unit 21 is disposed on an upper side 302 of the body 300. The collar 301 extends from a lower side 303 of the body 300. The body 300 has a front end 304 and a rear end 305. The collar 301 extends from the front end 304. The collar 301 extends from the body 300 at an acute angle to the longitudinal axis of the elongate body 300.

The collar 301 has an aperture 306 formed therethrough. The collar 301 is configured to receive the injection device 1 through the aperture 306. A channel 307 (refer to FIG. 6) is formed in the lower side 303 of the body 300. The channel 307 is elongate and extends between the front end 304 and the rear end 305 of the body 300.

Two wings 308, acting as protective walls, extend downwardly from the lower side 303 of the body 300. The wings 308 are spaced from each other and distend from either side of the channel 307. Therefore, the injection device 1 is receivable between the wings 308. The wings 308 are disposed at the rear end 305 of the body 300, at an opposite end of the body 300 to the collar 301.

The collar 301 and channel 307 form part of an alignment arrangement or alignment unit. The alignment unit is configured to locate the body in a specific position relative to the outside surface 106 of the injection device 1. The alignment unit forms part of the mating unit configured to embrace the housing 10 of injection device 1 to maintain the supplementary device in a specific position on the injection device 1.

The supplementary device 2 further includes an engaging unit or arrangement configured to releasably mount the body to the injection device 1. The collar 301 also forms part of the engaging unit. The engagement unit forms part of the mating unit.

The features that contribute to correct alignment of the supplementary device 2 on the injection device 1 can be termed an alignment arrangement or alignment unit. The features that contribute to engagement of the supplementary device 2 to the injection device 1 can be termed an engaging unit or engaging arrangement.

FIG. 4 shows a schematic view of the supplementary device 2 of FIG. 2a in a state where it is attached to injection device 1 of FIG. 1. With the housing 20 of supplementary device 2, a plurality of components are included. These are controlled by a processor 24, which may for instance be a microprocessor, a Digital Signal Processor (DSP), Application Specific Integrated Circuit (ASIC), Field Programmable Gate Array (FPGA) or the like. Processor 24 executes program code (e.g. software or firmware) stored in a program memory 240, and uses a main memory 241, for instance to store intermediate results. Main memory 241 may also be used to store a logbook on performed ejections/injections. Program memory 240 may for instance be a Read-Only Memory (ROM), and main memory may for instance be a Random Access Memory (RAM).

A supplementary memory 243 may also be used to store a logbook on performed ejections/injections. Program memory 240 may for instance be a Read-Only Memory (ROM), main memory 241 may for instance be a Random Access Memory (RAM), and supplementary memory 243 may for instance be a flash memory. The supplementary memory 243 may include part of the supplemental device 2 or may alternatively be removably couplable thereto by a USB-type interface for instance or other connection.

In an example embodiment, processor 24 interacts with a first button 22, via which supplementary device 2 may for instance be turned on and off. A second button 33 is a communications button. The second button may be used to trigger establishment of a connection to another device, or to trigger a transmission of information to another device. A third button 34 is a confirm or OK button. The third button 34 can be used to acknowledge information presented to a user of supplementary device 2. The buttons 22, 33, 34 may be any suitable form of user input transducers, for instance mechanical switches, capacitive sensors or other touch sensors.

Processor 24 controls a display unit 21, which is presently embodied as a Liquid Crystal Display (LCD). Display unit 21 is used to display information to a user of supplementary device 2, for instance on present settings of injection device 1, or on a next injection to be given. Display unit 21 may also be embodied as a touch-screen display, for instance to receive user input.

Processor 24 also controls an optical sensor 25, embodied as an Optical Character Recognition (OCR) reader, that is capable of capturing images of the dosage display 13, in which a currently selected dose is displayed (by way of numbers printed on the sleeve 19 contained in injection device 1, which numbers are visible through the dosage display 13). OCR reader 25 is further capable of recognizing characters (e.g. numbers) from the captured image and to provide this information to processor 24. Alternatively, the reader 25 in supplementary device 2 may only be an optical sensor, e.g. a camera, for capturing images and providing information on the captured images to processor 24. Then processor 24 is responsible for performing OCR on the captured images.

Processor 24 also controls light-sources such as light emitting diodes (LEDs) 29 to illuminate the dosage display 13, in which a currently selected dose is displayed. A diffuser may be used in front of the light-sources, for instance a diffuser made from a piece of acrylic glass. Furthermore, the optical sensor may include a lens (e.g. an aspheric lens) leading to a magnification (e.g. a magnification of more than 3:1)

Processor 24 further controls a photometer 26, that is configured to determine an optical property of the housing 10 of injection device 1, for example a colour or a shading. The optical property may only be present in a specific portion of housing 10, for example a colour or colour coding of sleeve 19 or of an insulin container included within injection device 1, which colour or colour coding may for instance be visible through an opening or window in housing 10 (and/or in sleeve 19). Information on this colour is then provided to processor 24, which may then determine the type of injection device 1 or the type of insulin contained in injection device 1 (e.g. SoloStar Lantus with purple colour and SoloStar Apidra with blue colour). Alternatively, a camera unit may be used instead of photometer 26, and an image of the housing, sleeve or insulin container may then be provided to processor 24 to determine the colour of the housing, sleeve or insulin container by way of image processing. Further, one or more light sources may be provided to improve reading of photometer 26. The light source may provide light of a certain wavelength or spectrum to improve colour detection by photometer 26. The light source may be arranged in such a way that unwanted reflections, for example by dosage display 13, are avoided or reduced. In an example embodiment, instead of or in addition to photometer 26, a camera unit may be deployed to detect a code (for instance a bar code, which may for instance be a one- or two-dimensional bar code) related to the injection device and/or the medicament contained therein. This code may for instance be located on the housing 10 or on a medicament container contained in injection device 1, to name but a few examples. This code may for instance indicate a type of the injection device and/or the medicament, and/or further properties (for instance an expiration date).

Processor 24 further controls (and/or receives signals from) an acoustic sensor 27, which is configured to sense sounds produced by injection device 1. Such sounds may for instance occur when a dose is dialed by turning dosage knob 12 and/or when a dose is ejected/injected by pressing injection button 11, and/or when a prime shot is performed. These actions are mechanically similar but nevertheless sound differently (this may also be the case for electronic sounds that indicate these actions). Either the acoustic sensor 27 and/or processor 24 may be configured to differentiate these different sounds, for instance to be able to safely recognize that an injection has taken place (rather than a prime shot only).

Processor 24 further controls an acoustical signal generator 23, which is configured to produce acoustical signals that may for instance be related to the operating status of injection device 1, for instance as feedback to the user. For example, an acoustical signal may be launched by acoustical signal generator 23 as a reminder for the next dose to be injected or as a warning signal, for instance in case of misuse. Acoustical signal generator may for instance be embodied as a buzzer or loudspeaker. In addition to or as an alternative to acoustical signal generator 23, also a haptic signal generator (not shown) may be used to provide haptic feedback, for instance by way of vibration.

Processor 24 controls a wireless unit 28, which is configured to transmit and/or receive information to/from another device in a wireless fashion. Such transmission may for instance be based on radio transmission or optical transmission. In some embodiments, the wireless unit 28 is a Bluetooth transceiver. Alternatively, wireless unit 28 may be substituted or complemented by a wired unit configured to transmit and/or receive information to/from another device in a wire-bound fashion, for instance via a cable or fibre connection. When data is transmitted, the units of the data (values) transferred may be explicitly or implicitly defined. For instance, in case of an insulin dose, always International Units (IU) may be used, or otherwise, the used unit may be transferred explicitly, for instance in coded form.

Processor 24 receives an input from a pen detection switch 30, which is operable to detect whether the pen 1 is present, i.e. to detect whether the supplementary device 2 is coupled to the injection device 1. A battery 32 powers the processor 24 and other components by way of a power supply 31.

The supplementary device 2 of FIG. 4 is thus capable of determining information related to a condition and/or use of injection device 1. This information is displayed on the display 21 for use by the user of the device. The information may be either processed by supplementary device 2 itself, or may at least partially be provided to another device (e.g. a blood glucose monitoring system).

The mating unit and mutually interacting engaging members of the injection device 1 and the supplementary device 2, such like for releasably mounting the supplementary device to the injection device in a specific position relative to an outside surface of the injection device will now be described in detail.

The correct alignment of the supplementary device 2 on the injection device 1 ensures that the OCR reader 25 is correctly aligned with the dosage window 13. Correct alignment allows correct operation and reliable readings. Ensuring that there can be correct alignment between the supplementary device 2 and the injection device 1 in use allows a simpler design for the OCR reader 25, in particular because it does not need to be designed to be able to accommodate different alignments between the devices 1, 2.

Figure 5:
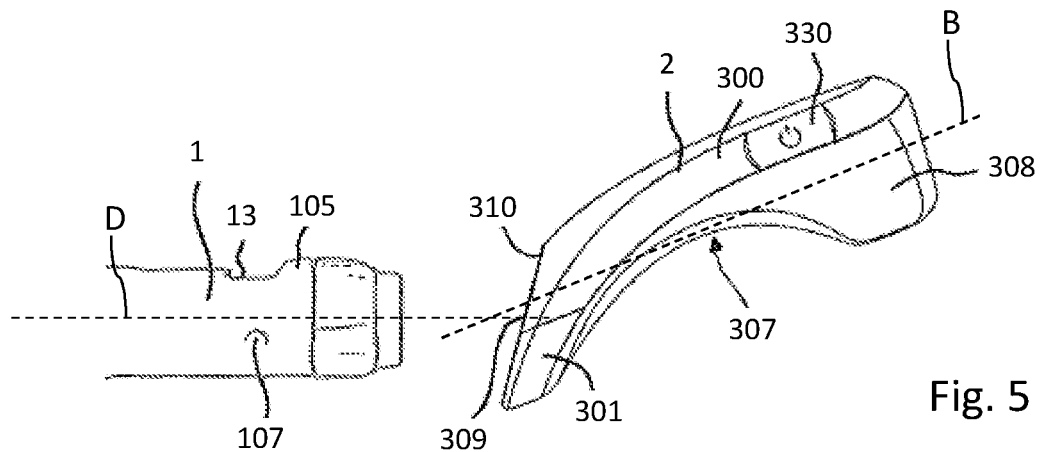
FIG. 5 shows a perspective side view of the supplementary device oriented to be mounted to the injection device.

Referring to FIG. 5, the supplementary device 2 is shown prior to mounting the supplementary device 2 on the injection device 1. In FIG. 5, the supplementary device 2 is shown orientated relative to the rear section 102 of the housing 10 of the injection device 1 so that the rear section 102 is receivable through the aperture 306 formed in the collar 301.

The housing 20 of the supplementary device 2 includes the body 300 and the collar 301. The elongate body 300 has a longitudinal axis, with the collar 301 distending downwardly from the front end 304 of the body 300. The channel 307 (refer to FIGS. 7 and 8) formed in the lower side 303 of the body 300 extends from the aperture 306 formed in the collar 301. Therefore, an upper portion of the aperture 306 forms part of the elongate channel extending between the front end and the rear end of the housing 20.

The aperture 306 has a front opening 309. The front opening 309 is formed in a front face 310 of the housing 20. The front face 310 may be planar. The edge of the front opening 309 is defined on a plane extending at an angle to the longitudinal axis of the elongate body 300. The front opening 309 has an elliptical shape. The width of the front opening 309 at its minor axis or conjugate diameter corresponds to or is slightly greater than the diameter of the rear section 102 of the injection device 1. The width of the front opening 309 at its major axis or transverse diameter is greater than the diameter of the rear section 102 of the injection device 1. It will be understood that the rear section 102 of the injection device 1 is receivable through the opening 309 so that it extends through the aperture 306.

Figure 7:
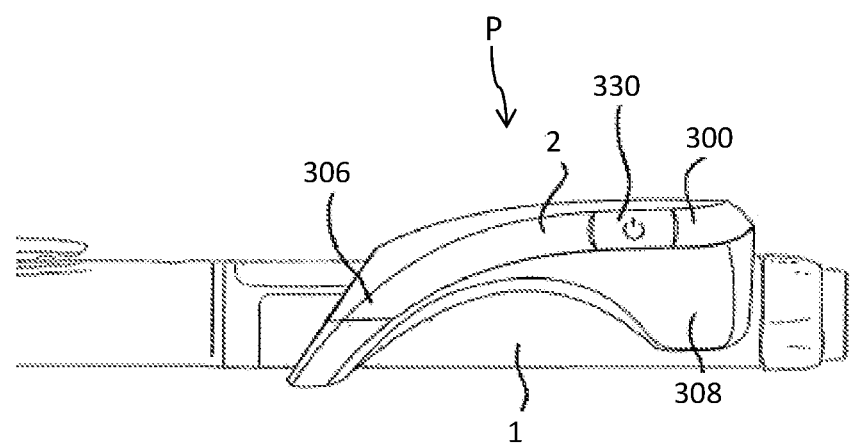
FIG. 7 shows a side view of the supplementary device releasably attached to the injection device.
Figure 9:
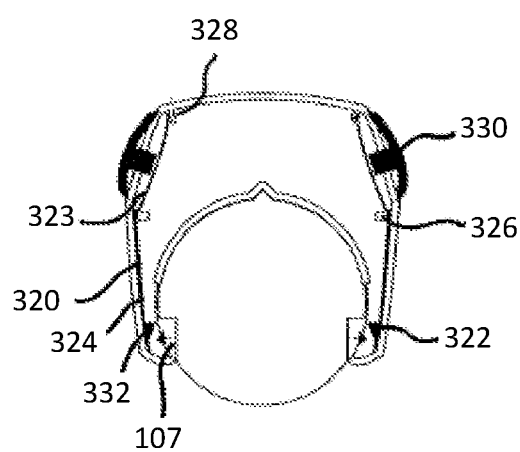
FIG. 9 shows a cross-sectional rear view of the supplementary device releasably attached to the injection device with resilient arms of a fixing unit in a disengaged position with the injection device.

The channel 307 is shown in FIGS. 7 to 9. The channel 307 has a base 312. The base 312 of the channel 307 is arcuate in cross-section. The base 312 extends parallel to the longitudinal axis of the body 300. The shape of the base 312 corresponds to the outer surface of the rear section 102 of the injection device 1. Therefore, the rear section 102 of the injection device is receivable therein and the outer surface of the injection device 1 locates against the channel base 312. The optical sensor 25 is embedded in the channel base 312 to face into the channel 312.

The collar 301 defines an upper part 314 and a lower part 315. The upper part 314 is integrally formed with the body 300 and thus extends from the base 312 of the channel 307. The lower part 315 opposes, but is at least partially offset from, the upper part 314. In the present embodiment, the upper part 314 is defined by the upper half of the inner surface of the collar 301 and the lower part 315 is defined by the lower half of the inner surface of the collar 301. The inner surface of the collar 301 defines a cylinder, with the base 312 of the channel 307 extending from the cylindrical surface. Therefore, the arcuate base of the channel 307 and the inner cylindrical surface of the collar are formed to arc about the same longitudinal axis.

A lower locating surface 317 is defined on the lower part 315 of the collar 301. An upper locating surface 316 is defined on the upper part 314 of the collar 301. The upper and lower locating surfaces oppose each other. When the injection device is received through the aperture, the upper and lower locating surfaces 316, 317 are configured to locate against the outer surface of the injection device 1. the locating surfaces 316, 317 are brought into contact with the injection device 1 by rotating the supplementary device 2 about an axis extending perpendicular to the major axis of the opening 309 so that the upper and lower locating surfaces are moved towards the outer surface of the injection device 1. The central axis of the cylindrical aperture extending through the collar is brought into co-axial alignment with the longitudinal axis of the injection device 1.

In the present embodiment, the base 312 of the channel extends co-planar with the upper part of the collar 301. Therefore, the base 312 of the channel also locates against the outer surface of the injection device 1 when the supplementary device 2 is rotated about an axis extending perpendicular to the major axis of the opening 309 so that the upper and lower locating surfaces are moved to lie against the outer surface of the injection device 1. Therefore, it will be understood that the upper locating surface may be formed by the upper part 314 of the collar, or by the base 312 of the channel 307. Alternatively, the lower locating surface is formed on one or more locating elements protruding into the aperture from the lower part of the collar. Similarly, the upper locating surface is formed on one or more locating elements protruding into the aperture or the injection device receiving channel.

A rib receiving recess 318 (refer to FIGS. 8 and 9) is formed in the base 312 of the channel 307. The rib receiving recess 318 is dimensioned to receive the rib 105 protruding from the outer surface 106 of the injection device 1. The rib receiving recess 318 is dimensioned so as to correspond closely to the shape and size of the locating rib 105 that is present on the injection pen 1. The rib receiving recess 318 is slightly larger than the locating rib 105 so as to ensure that the locating rib 105 can be easily located within the recess. Therefore, the rib 105 acts as an alignment element for locating the body in a specific position relative to the outer surface 106 of the injection device 1 when the rib 105 is received in the rib receiving recess 318. The rib receiving recess 318 therefore aids the correct alignment and orientation of the body 300 on the injection device 1.

The rib receiving recess 318 is formed at the end of the supplementary device 2 that is closest to the dosage knob 12 when the supplementary device 2 is fitted to the injection device 1. Left and right arms 320, acting as support members, extend below the injection device receiving channel 307 on left and right sides of the body 300. As shown in FIGS. 8 and 9, a lower part 324 of each arm 320 depends substantially vertically from the lower side of the body 300 of the supplementary device 2. Therefore, the arms 320 extend either side of the injection device receiving channel 307 and are spaced from each other.

The left arm 320 has a left protuberance 322 disposed at a free end 321 of the lower part 324. The right arm 320 also has a right protuberance 322 disposed at a free end 321 of the lower part 324. Each protuberance 322 acts as an engaging element to engage in the indents 107 formed in the outer surface of the rear section 102 of the injection device 1. The protuberance 322 on the left arm 320 is configured to be received in the left indent 107. The protuberance 322 on the right arm 320 is configured to be received in the left indent 107. The protuberances 322 are shaped to correspond to the shapes of the indents 107 respectively. In this way, the protuberances 322 fit within the corresponding indents 107 respectively when the supplementary device 2 is correctly positioned on the injection device 1. The external dimensions of the protuberances 322 are slightly smaller than the internal dimensions of the indents 107 so as to ensure that the protuberances 322 fit within their respective indent.

In the present embodiments, the right protuberance 322 is shaped to correspond closely to the shape of the right indent 107. In this way, the right protuberance 322 fits snugly within the right indent 107 when the supplementary device 2 is correctly positioned on the injection pen 1. The left protuberance 322 is shaped similarly to the right protuberance 322, although it is less tall. Put another way, it is like the right protuberance 322 but with the top part is missing or cut off. This is the reason for the end face of the left protuberance 322 having a larger area than the right protuberance 322. The different sizes for the protuberances 322 helps the protuberances find engagement within the indents 107. The right protuberance 322 can be considered to be a master to the left protuberance 322, which is a slave.

5

Each arm 320 has an upper part 323 and a lower part 324. A step 325 is formed at a mid section of each arm 320, with the upper part 323 depending from one side of the step 325 and the lower part 324 depending from the other side. The protuberance 322 is formed at the free end of the lower part 324. The lower part 324 extends from the step 325 at an angle to the upper part 323.

A support element 326 is disposed in the left side of the body 300. Another support element 326 is disposed in the right side of the body 300. Each support element 326 is disposed in the body 300 and spaced from an outer shell 327 of the body 300 to define a gap. The left arm 320 is received in a left side of the body 300. The right arm 320 is received in a right side of the body 300. The arms 320 are disposed behind the wings 308 that depend from the body 300. The wings 308 may be formed from a transparent material. This allows a user to be able to view the locations of the arms 320 relative to the indents 107, which may help the user to locate the supplementary device 2 correctly on the injection device 1.

As can be seen from FIG. 8, the wings, or protective walls 308, extend slightly further in a downwards direction than the arms. The left arm 320 extends through the gap formed in the left side of the body 300 and the right arm 320 extends through the gap on the right side of the body 300. The step 325 formed at the mid-section of each arm 320 locates against the corresponding support element 326. The step 325 locates each arm 320 so that the lower part 324 extends below the support element 326. The end of the upper part 323 of each arm 320 locates against a tab 328 extending from an inner surface of the body outer shell 327. The upper part 323 of each arm 320 is therefore retained in position in the body 300 and extends between the support element 326 and the tab 328.

The distance between each support element 326 and tab 328 is slightly less than the length of the upper part 323 of each arm 320. Therefore, when the upper part 323 of each arm 320 is disposed between the corresponding element 326 and the tab 328, the upper part 323 of each arm 320 is deformed to have an arcuate shape. Each arm 320 is resilient. The upper part 323 bows into a convex shape towards the outer shell of the body 300. Therefore, the step 325 is biased against the support element 326 and the free end of the upper part 323 is biased against the tab 328. The upper part 323 of each arm 320 between the free end and the step is urged towards the outer shell 327.

The lower part 324 of each arm 320 extends from the upper part 323 and through the gap defined between the support element 326 and the outer shell 327. The lower parts 324 of the arms 320 are splayed towards each other, extending from the support element 326. The effect of the resilience of the upper part 323 of each arm 320 is to bias the lower part 324 of each arm 320 into a certain position. The position into which the lower part 324 of each arm 320 is initially located is such that the distance between the innermost surfaces of the protuberances 322 is slightly less than the distance between the bottoms of the indents 107. The effect of the bias of each arm 320 is to resist movement of the protuberances 322 and the lower parts 324 of the arms 320 away from one another.

The arms 320, acting as support members, are restrained from moving in a direction along the longitudinal axis of the elongate body 300. This assists in maintaining the supplementary device 2 in the correct location after engagement of the supplementary device on the injection pen 1 even in the presence of forces acting to move the supplementary device 2 along the longitudinal axis of the injection pen 1. The arms 320 can be termed support members because they support the protuberances.

Left and right buttons 330 are mounted on the left and right sides of the body 300. An aperture 331 is formed through the outer shell 327 on each side of the body 300. A protrusion, acting as an actuating element 332, is formed on the rear side of each button 330 and extends through the corresponding aperture 331 to act on the upper part 323 of the corresponding arm 320 and apply a biasing force thereon.

When one of the buttons 330 is pressed inwardly by a user the actuating element 332 of each button 330 is biased inwardly. The actuating element 332 urges against the convex surface of the upper part 323 of the corresponding arm 320. The upper part 323 then deforms under the force applied by the actuating element 332. The support element 324 acts as a fulcrum and the arm 320 is urged to pivot about the support element. The distal end of the upper part 323 is prevented from moving by the tab 328 against which the upper part 323 is located. However, the free end 321 of the lower part 324 is free to move outwardly and so the lower part 324 pivots about the support element 324.

When both buttons 330 are pressed, the lower parts 324 of the two arms 320 are urged to rotate about their respective support elements 324. Therefore, the free ends 321 of the arm lower parts 324 are urged away from each other. The release of the pressing force on each button releases the biasing force acting on the upper part 323 of each arm and so the lower part of each arm is urged to return to its neutral position due to the resilience of the arms 320.

As is shown in FIG. 5, the supplementary device 2 is initially located with respect to the injection pen 1 such that the opening 309 to the aperture 306 in the collar 301 is aligned with the rear end of the injection device 1. The body 300 is orientated so that the longitudinal axis B of the injection device receiving channel 307 is inclined with respect to the longitudinal axis D of the injection device 1.

Figure 6:
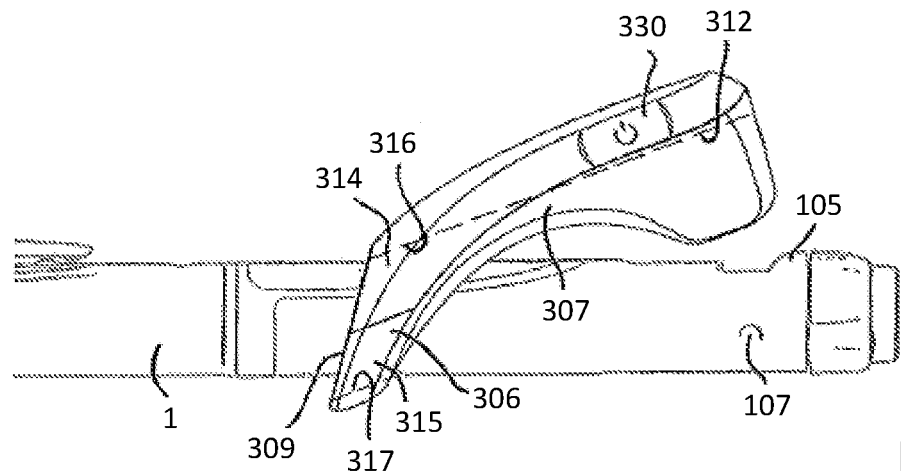
FIG. 6 shows a side view of the supplementary device with the injection device received through a collar of the supplementary device.

The collar 301 is then slid over the rear section 102 of the injection device 1, as shown in FIG. 6. The width of the front opening 309 at its minor axis or conjugate diameter corresponds to or is slightly greater than the diameter of the rear section 102 of the injection device 1. The width of the front opening 309 at its major axis or transverse diameter is greater than the diameter of the rear section 102 of the injection device 1. Therefore, the rear section 102 of the injection device 1 is received through the aperture 306 of the collar 301.

In order to locate the supplementary device 2 on the injection device 1, the supplementary device 2 is rotated relative to the injection device 1 about the transverse axis T extending perpendicular to the major axis of the opening 309, hence the longitudinal axis B of the supplementary device 2. The longitudinal axes D of the injection device 1 and the injection device receiving channel 307 are rotated towards each other. Furthermore, the upper and lower locating surfaces 316, 317 are moved towards the outer surface of the injection device 1.

As the supplementary device 2 and injection device 1 are rotated relative to each other the free ends 321 of the right and left arms 320, in particular the protuberances 322, brought into contact with the outer surface of the injection device housing 10. The protuberances 322 here contact the housing to the left and right sides of the display window 13.

In order to engage the supplementary device 2 with the injection device 1, the user first arranges the supplementary device 2 with respect to the injection device 1 as shown in FIG. 6, and then applies a further force downwards on the supplementary device 2 while at the same time applying a force upwards on the injection device 1. Therefore, the supplementary device 2 and injection device are urged to rotate relative to each other about the collar 301. A biasing force is therefore applied to the protuberances 322 by the outer surface of the rear section 102. As the injection device 1 and the supplementary device 2 are urged to move closer together, the biasing force results in the arms being urged away from each other.

The lower part 324 of each arm 322 is urged to deflect outwardly, and to pivot about the corresponding support element 326. However, the upper part 323 of each arm is prevented from pivoting by the corresponding tab. This causes a reaction force to be applied by the lower part 324 of each arm due to the resilience of each arm 320, which resists entry of the injection device 1 into the injection device receiving channel 307. However, as the supplementary device 2 is further rotated over the injection device 1, the protuberances 322 become aligned with the left and right indent 107 and, due to the resilience of the arms 320, engage with the indents 107.

Referring to FIG. 7, as the supplementary device 2 is further rotated with regard to the transverse axis T to engage the protuberances 322 in the indents 107, the rear section of the injection device 1 is received in the injection device receiving channel 207. The lower locating surface 317 of the collar 301 is urged into contact with a lower side of the outer surface of the injection device 1 and the upper locating surface 316 is urged into contact with an opposing side of the outer surface of the injection device 1. Once the protuberances 322 engage in the indents 107, there is significant resistance to further movement of the supplementary device 2 relative to the injection device 1, due in part to the lower and upper locating surfaces 316, 317 abutting the outer surface of the injection device. The upper and lower locating surfaces 316, 317 are partially offset from each other, with the upper locating surface 317 being disposed between the lower locating surface and the protuberances 322. Movement of the supplementary device 2 relative to the injection device 1 in the opposite direction is restricted by the protuberances 322 being engaged in the indents 107. The injection device 1 also locates against the base 312 of the channel 307.

It will be understood that the body 300 is mated to the injection device 1 by the collar 301 extending circumferentially around the injection device 1 at a front end of the body 300, and the protuberances 322 engaging in the indents 107 at the rear end of the body 300.

In order to properly align and to properly orient the supplementary device 2 with regard to the injection device 1 the supplementary device 2 as shown in FIG. 10 includes at least one indicator 350, 380 having a shape or contour to overlap or to align with a correspondingly-shaped mark 150, 180 on the outside surface 106 of the injection device 1 when the body 300 is in or near the specific position P, as shown in FIG. 7, in which the mutually-corresponding engaging members 340, 140 of the body 300 and the injection device 1 are configured and mutually arranged to releasably engage the supplementary device 2 with the housing 10 of the injection device 1.

As further illustrated in FIG. 10 the supplementary device 2 is further equipped with an optical reading arrangement 334 at its lower side 303. A tangential or circumferential as well as a longitudinal distance between the optical reading arrangement 334 to the indicator 350 matches with a distance between the mark 150 and the display 13 of the injection device 1. In this way it is almost guaranteed that the optical reading arrangement 334 is correctly positioned over or across the display 13 when the indicator 350 overlaps with the mark 150.

Figure 12:
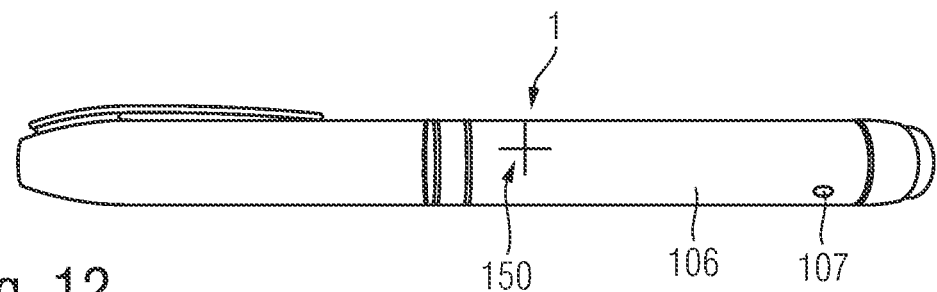
FIG. 12 shows another embodiment of the injection device with a different mark.
Figure 16:
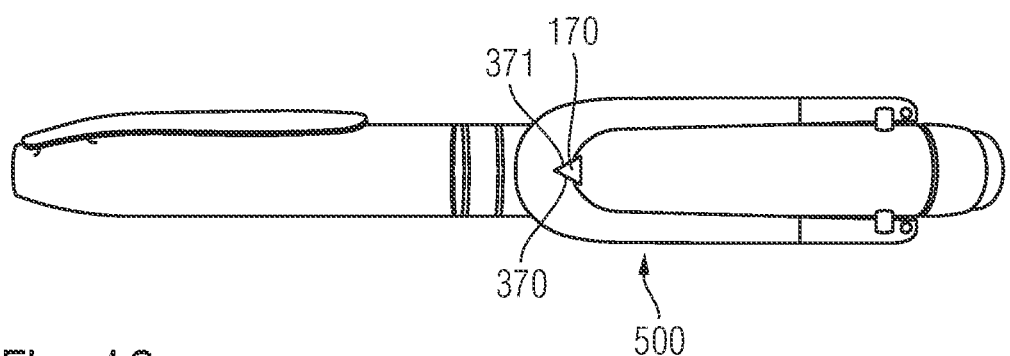
FIG. 16 shows an assembly of the supplementary device of FIG. 14 with the injection device of FIG. 15.
Figure 17:
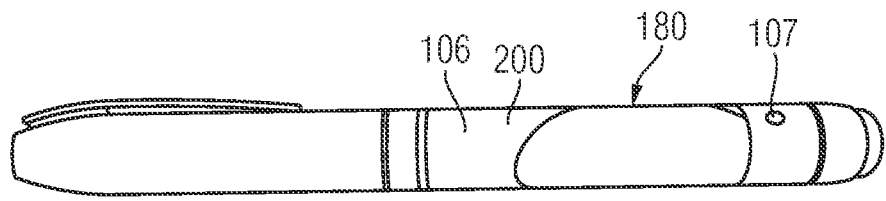
FIG. 17 shows a side view of another injection device with a mark on its outside surface.

In FIGS. 11 and 17 two different examples of a mark 150, 180 on the outer circumference or on the outside surface 106 of the injection device 1 are illustrated. In FIG. 12, an alternative embodiment of a visible mark 160 is shown. The mark 150 as illustrated in FIG. 11 includes a circular symmetric structure, e.g. in form of a circle that matches in shape and size with the circular symmetric indicator 350 located or provided in the lower part 315 of the collar 301. Due to the mutually corresponding indicators 350, 370, 380 and marks 150, 160, 170, 180 as shown in the various embodiments of FIGS. 10-18 a correct and well-defined mutual alignment of the supplementary device 2 with regard to the injection device 1 can be obtained in a preassembly configuration as shown in FIG. 6, namely in which the injection device 1, in particular its housing 10 is received in the collar 301 and intersects the aperture 306 thereof.

In this preassembly configuration the injection device 1 is rotatable with regard to its longitudinal axis D until the tangential or circumferential position of the mark 150, 160, 170, 180 substantially overlaps with the tangential or circumferential position of the indicator 350, 370, 380. Prior to, simultaneous with or after such a rotation it is also possible to slide the injection device 1 in longitudinal direction inside or through the aperture 306 of the collar 301 so as to align the at least one mark 150, 160, 170, 180 with the correspondingly-shaped indicator 350, 370, 380 with regard to the longitudinal direction. When the indicator 350, 370, 380 substantially overlaps with the correspondingly-shaped mark 150, 160, 170 or 180 the rear end 305 of the body 300 is to be urged towards the injection device 1, thereby pivoting the supplementary device 2 as shown in FIG. 6 in clockwise direction with regard to the transverse axis T to arrive in a final assembly configuration and in the specific position P as shown in FIG. 7.

Since the indicator 350, 370, 380 is correctly aligned with the corresponding mark 150, 160, 170, 180 the mutually corresponding engaging members 340, 140 of the supplementary device 2 and the injection device 1 engage with each other. In the embodiments as shown in FIGS. 3-18 the engaging members 340 of the supplementary device 2 are provided by radially inwardly extending protuberances 322 to engage with engaging members 140 of the injection device 1 being configured or implemented as the indents 107. Apart from the illustrated embodiment there are many different configurations of mutually corresponding engaging members 340, 140 of supplementary device 2 and injection device 1 conceivable, such like arbitrary snap-fit members or clipping members.

The mutual alignment of the at least one indicator 350 with regard to the at least one mark 150 is obtainable prior to arrange the supplementary device 2 in a final assembly configuration as shown in FIG. 7. Correct alignment of the indicator 350 overlapping with the mark 150 the pivoting of the supplementary device 2 from the preassembly configuration towards the end assembly configuration inevitably leads to a precise and reliable mutual engagement of protuberances 322 and indents 107 as well as to a precise alignment of the rib 105 with the rib-receiving recess 318.

Figure 13:
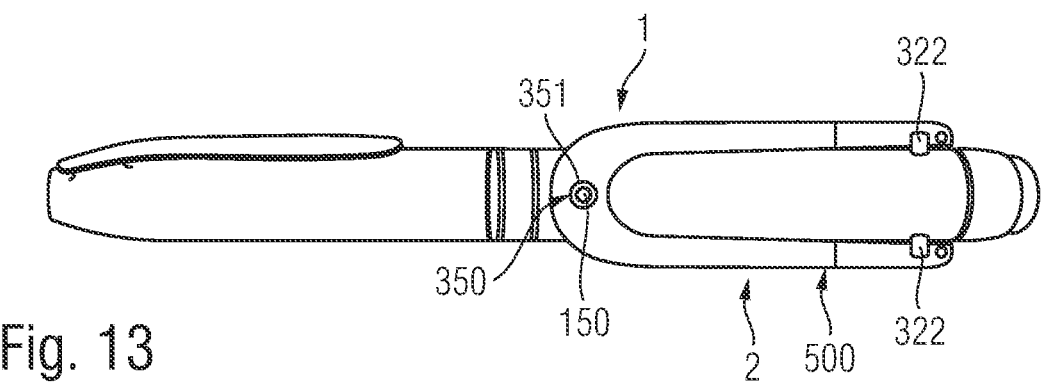
FIG. 13 shows the injection device of FIG. 11 with the supplementary device of FIG. 10 attached thereto.

In the embodiment as shown in FIGS. 10, 11 and 13 the indicator 350 is configured as a through opening in the bulk of the collar 301 of the body 300. Alternatively it is conceivable that the indicator 350 is formed by a transparent window allowing to visualize the mark 150 located underneath. Implementation and use of mutually corresponding indicators 350, 370, 380 with respective marks 150, 160, 170, 180 is of particular benefit when the body 300 of the supplementary device 2 is substantially non-transparent so that the mutually engaging members 340, 140 of the supplementary device 2 and of the injection device 1 are not visible during the assembly process. But even if the body or portions thereof would be substantially transparent it is of particular benefit to have at least one indicator on the body to overlap or to align with a mark on the outside surface 106 of the injection device 1 prior to an end assembly.

In an alternative but not illustrated embodiment it is conceivable, that both, the indicator 350 and the mark 150 include somewhat identical marks that have to be arranged in an overlapping configuration.

Figure 14:
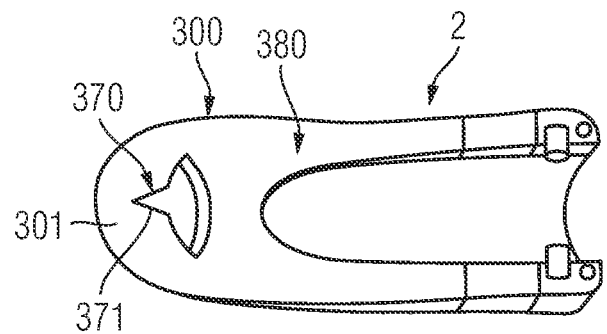
FIG. 14 shows another embodiment of the supplementary device with a differently-shaped indicator.
Figure 15:
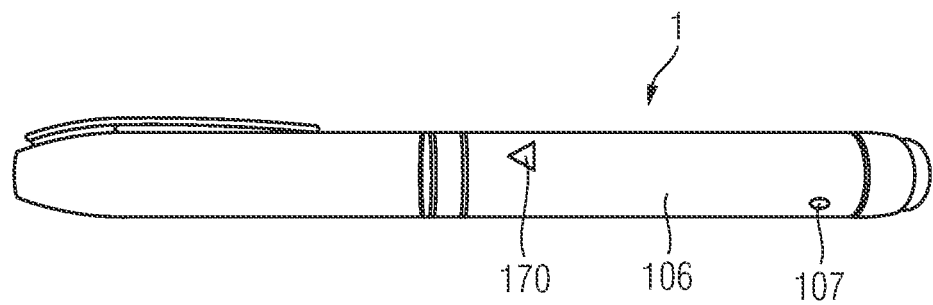
FIG. 15 shows a side view of a further embodiment of the injection device with a mark matching with the indicator according to FIG. 14.

In the embodiment according to FIG. 12, the circular symmetric mark 150 as shown in FIG. 11 is replaced by a mark 160 featuring a cross shape. There, the center of the crossed structure has to be brought in overlapping arrangement with the center of the aperture 351 of the indicator 350. In the further embodiment as shown in FIGS. 14-16 the mark 170 on the outside surface 106 of the injection device 1 is of triangular shape to match with a triangularly-shaped or V-shaped recess 371 in the collar 301 of the body 300 of a supplementary device 2 as shown in FIG. 14. There, the recess 371 is provided at a margin or border of the lower part 315 of the collar 301.

Arranging the indicator 350, 370 in the collar 301 of the body 300 is of particular benefit since the collar is overlapping with the transverse axis T serving as a pivot or rotation axis for transferring the supplementary device 2 from a preassembly configuration as shown in FIG. 6 into the end assembly configuration as shown in FIG. 7. The relative movement of the collar 301 and hence of the indicator 350, 370 with regard to the mark 150, 160, 170 is rather small compared to the relative displacement of the body's rear end 305 with regard to the injection device 1.

Figure 18:
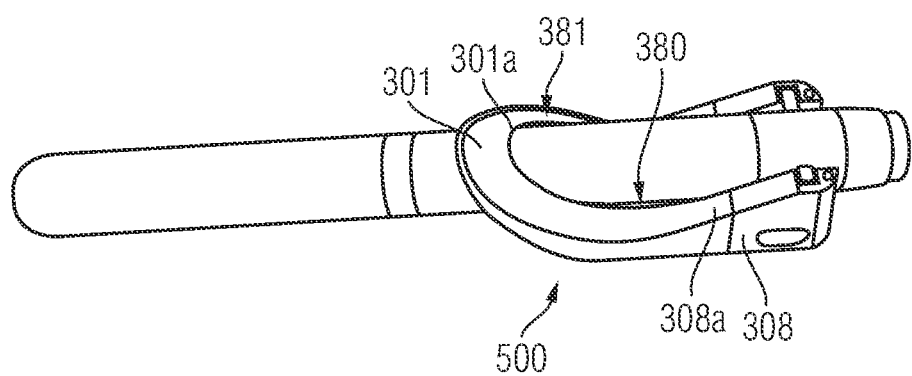
FIG. 18 shows an assembly of the supplementary device with the injection device according to FIG. 17.

In the further embodiment as shown in FIGS. 17 and 18 the mark 180 on the outside surface 106 of the injection device 1 includes an oval or oval-like structure and matches with the inside-facing border 301a of the collar 301 and a lower border 308a of the wings 308. As shown in FIG. 18 the wings 308, in particular the radially inwardly-facing border 308a thereof smoothly extends into the border 301a of the collar 301 facing towards the second longitudinal end or to the rear end 305. As shown in FIG. 18 and when arriving in the end assembly configuration the shape of the border line of the collar 301 and the wings 308 almost exactly match with the contour of the mark 180 provided on the outside surface 106 of the injection device 1. In this embodiment the borders 301a, 308a form a sidewall structure of the body 300 that is interpretable as a recess obtained by cutting away a portion of a somewhat tubular-shaped body 300. In this way, the border formed by the wings 308 and the collar 301 are to be considered as a recess in a sidewall of a tubular-shaped body through which the outside surface 106 of the injection device 1 is visible.

Any marks 150, 160, 170 and 180 as shown in the various FIGS. 11-18 can either be implemented as visual marks or haptic marks. Haptic marks may protrude from the outside surface 106 to such a degree that they are perceptible by the fingers of a user so as to facilitate correct alignment and assembly of the supplementary device 2 and the injection device 1. The combination and mutual arrangement of the supplemental device 2 with the injection device constitutes a kit 500. Such a kit 500 may be initially delivered or handed out to a patient. With to releasable engagement of the supplemental device 2 and the injection device a used injection device of the kit 500 may be replaced by new one if requested.

For a simple and universal practical implementation it is conceivable that the mark 150, 160, 170 or 180 is integrated into a label 200 that is adhesively attachable to the outside surface 106 of the injection device 1, in particular to the housing 10 thereof. The label 200 as shown in FIG. 17 may include a plastic, foil or laminated foil and may be completely or in sections adhesively attached to the housing 10 of the injection device 1.

REFERENCE NUMBERS

1 injection device
2 supplementary device
10 housing
11 injection button
12 dosage knob
13 display
14 container
15 needle
16 inner needle cap
17 outer needle cap
18 protective cap
18a lip
20 housing
20-1 clip feature
20-2 clip feature
21 display unit
22 button
23 signal generator
24 processor
25 OCR reader
26 photometer
27 acoustical sensor
28 wireless unit
29 LED
30 detection switch
31 power supply
32 battery
33 button
34 button
140 engaging member
150 mark
160 mark
170 mark
180 mark
200 label
240 program memory
241 main memory
300 body
301 collar
301a border
302 upper side
303 lower side
304 front end
305 rear end
306 aperture
307 channel
308 wing
308a border
309 front opening
310 front face
312 base
314 upper part
315 lower part
316 upper locating surface
317 lower locating surface
318 recess
320 arm
321 free end
322 protuberance
323 upper part
324 lower part
325 step
326 support element
327 body outer shell
328 tab
330 button
332 actuating element
334 optical reading arrangement
340 engaging member
350 indicator
351 aperture
370 indicator
371 recess
380 recess
381 recess
500 kit

The invention claimed is:

1. A supplementary device for a manually operable injection device, the injection device comprising a housing configured to receive a medicament container inside the housing, the supplementary device comprising:
a body having at least one engaging member to releasably mount the body to the housing of the injection device in a specific position on an outside surface of the housing of the injection device;
a unitary collar integrally formed with the body, the collar comprising a closed ring structure and a collar aperture confined by the closed ring structure, the collar aperture being sized to receive the housing of the injection device through the collar aperture; and
at least one indicator arranged on the collar, located within the closed ring structure and having a shape or contour to overlap or to align with a mark on the outside surface of the housing of the injection device when the body is in or near the specific position,
wherein the at least one indicator is located offset from the at least one engaging member, and wherein the at least one indicator comprises an aperture in the body, the aperture reveals a section of the outside surface of the housing of the injection device when the supplementary device and the injection device are in a preassembly configuration.

2. The supplementary device according to claim 1, wherein a contour of the aperture matches with a shape of the mark.

3. The supplementary device according to claim 1, wherein the at least one indicator comprises a recess in the body.

4. The supplementary device according to claim 3, wherein the contour of the at least one indicator matches with the shape of the mark.

5. The supplementary device according to claim 3, wherein the recess is located in a margin or border of the body.

6. The supplementary device according to claim 5, wherein the recess comprises a V-shaped geometry with a pointed tip extending away from the border or margin.

7. The supplementary device according to claim 1, wherein the collar extends from a first longitudinal end and from a lower side of the body, and wherein the at least one engaging member is located at or near a second longitudinal end of the body opposite to the first longitudinal end.

8. The supplementary device according to claim 1, wherein the at least one indicator is formed by a transparent window allowing visualization of the mark located underneath.

9. The supplementary device according to claim 1, wherein the at least one indicator is configured as a through opening in a bulk of the collar of the body.

10. The supplementary device according to claim 1, wherein the collar aperture has a front opening and wherein the front opening is formed in a front face of the body.

11. The supplementary device according to claim 10, wherein the front face is planar.

12. The supplementary device according to claim 10, wherein the front opening has an elliptical shape.

13. The supplementary device according to claim 12, wherein a width of a minor axis or a conjugate diameter of the front opening corresponds to or is slightly greater than a diameter of a rear section of the housing of the injection device and wherein a width of a major axis or a transverse diameter of the front opening is greater than the diameter of the rear section of the housing of the injection device.

14. The supplementary device according to claim 1, wherein the body comprises an upper side and a lower side opposite to the upper side, wherein the lower side faces towards an outside surface of the housing of the injection device when the supplementary device is mounted to the housing body of the injection device.

15. The supplementary device according to claim 14, wherein the unitary collar extends from the lower side of the body and defines an upper part and a lower part, wherein the upper part adjoins the body, and wherein the at least one indicator is located in or on the lower part.

16. The supplementary device according to claim 1, wherein the at least one indicator is located circumferentially offset from the at least one engaging member as seen with respect to a tubular structure of the body.

* * * * *

UNITED STATES PATENT AND TRADEMARK OFFICE
CERTIFICATE OF CORRECTION

PATENT NO. : 10,888,667 B2
APPLICATION NO. : 15/551985
DATED : January 12, 2021
INVENTOR(S) : Stephan Riedel and Pauline Mannechez Page 1 of 1

It is certified that error appears in the above-identified patent and that said Letters Patent is hereby corrected as shown below:

On the Title Page

Column 1, Line 1 of PCT Pub. Date:, delete "Feb. 5, 2016" and insert -- August 25, 2016 --

In the Claims

Column 28, Line 21, Claim 14, after "housing", delete "body"

Signed and Sealed this
Thirtieth Day of March, 2021

Drew Hirshfeld
*Performing the Functions and Duties of the
Under Secretary of Commerce for Intellectual Property and
Director of the United States Patent and Trademark Office*